United States Patent [19]

Mann

[11] Patent Number: 4,491,561

[45] Date of Patent: Jan. 1, 1985

[54] DENTAL ALLOY

[75] Inventor: Douglass M. Mann, Westport, Conn.

[73] Assignee: CMP Industries, Inc., Albany, N.Y.

[21] Appl. No.: 531,429

[22] Filed: Sep. 12, 1983

[51] Int. Cl.$^3$ ............................................. C22C 19/07
[52] U.S. Cl. ................................... 420/437; 433/207; 433/222
[58] Field of Search ................ 420/437, 440; 148/425; 433/207, 222

[56] References Cited

U.S. PATENT DOCUMENTS 4,459,263  7/1984  Prasad ................................. 420/437

Primary Examiner—R. Dean
Attorney, Agent, or Firm—Bert J. Lewen

[57] ABSTRACT

A new chromium-cobalt dental alloy having a low coefficient of expansion, high oxidative stability, and easy workability is disclosed. The alloy contains 55 to 65 wt. % cobalt, 16 to 24 wt. % chromium, and controlled percentages of molybdenum and vanadium.

4 Claims, No Drawings

DENTAL ALLOY

BACKGROUND OF THE INVENTION

It has long been desired to develop alloys other than costly gold or other precious metals for use in the fabrication of metal tooth caps used as a base for porcelain application. For a period, nickel-chromium alloys containing small percentages of beryllium were used successfully; however, because of concern over allergic reactions to nickel and beryllium, such alloys are considered by some to be health hazards. As a matter of fact, certain countries have banned completely the use of these metals in dental alloys.

More recently, research has been undertaken to improve chromium-cobalt alloys, alloys which have been used for removable partial dentures since the 1930s, so that they could be used for porcelain application to form permanent dental structures. The generally used formulation of such alloys contains about 66% cobalt, 27% chromium, 5.5% molybdenum, 0.75% each of manganese and silicon, and 0.40% carbon. To date, however, such chromium-cobalt alloys suffer from several drawbacks making them unsuitable for the desired commercial applications. Firstly, the alloy expands too much during the process of baking porcelain to it, causing the porcelain to craze. These alloys have a minimum coefficient of expansion at 575° C. of 14.1, an amount not quite within the limit of acceptability for baking porcelain to them. Secondly, chromium and cobalt oxides form on these alloys during baking, causing the porcelain to discolor. This enhances the likelihood of porcelain cracking and poor adhesion. Thirdly, the chromium-cobalt alloys are very hard, making finishing and polishing extremely difficult and labor-intensive. Finally, and also of significant importance, the chromium-cobalt alloys are higher fusing than nickel chromium and consequently exhibit considerable shrinkage after casting, resulting in poor-fitting crowns.

Several attempts have been made to overcome these deficiencies. For example, up to 10% tungsten has been added to the chromium-cobalt alloys to reduce the coefficient of expansion, and aluminum and columbium as well as rhenium and ruthenium have been used to reduce oxidation. While such alloys have resolved some of the problems, the fusing temperature of the resulting alloy is quite high which results in after-casting shrinkage and poor fit and hardness also remains a problem.

BRIEF DESCRIPTION OF THE INVENTION

In order to overcome the foregoing problems, it has been discovered that a chromium-cobalt alloy having from 55 to 65% cobalt, 16 to 24% chromium, 6 to 8% molybdenum, and 2 to 4% each of aluminum and vanadium is suitable for the preparation of dental structures. It is also desirable that the alloys of the invention have less than one-tenth of a percent of carbon. The presence of iron is also advantageous. The foregoing compositions have coefficients of expansion at 575° C. of less than 14, a range which is adequate for use with porcelain. Additionally, these compositions have little tendency to oxidize and have relatively low fusion temperatures thereby resulting in low after-casting shrinkage.

DETAILED DESCRIPTION OF THE INVENTION

Compositions of the alloys of the invention are set forth below in the following table:

TABLE 1

| Component | Broad Range | Preferred Range |
| --- | --- | --- |
| Cobalt | 55–65% | 56–60% |
| Chromium | 16–24% | 18–22% |
| Molybdenum | 6–8% | about 7.5% |
| Aluminum | 2–4% | about 3% |
| Vanadium | 2–4% | 3–3.5% |
| Silicon | under 1% | under 1% |
| Manganese | under 1% | under 1% |
| Carbon | under .1% | under .1% |
| Iron | 0–10% | 5–8% |

The following examples demonstrate the advantages of the alloy of the instant invention.

EXAMPLE 1

A series of alloys were prepared and their coefficients of expansion at 575° C. measured. In the table below, the amounts are set forth in parts by weight.

TABLE 2

| Component | CC1 | CC2 | CC3 | CC4 | CC5 |
| --- | --- | --- | --- | --- | --- |
| Cobalt | 66 | 66 | 71.5 | 82.5 | 58.5 |
| Chromium | 27 | 27 | 27 | 16 | 20 |
| Molybdenum | 5.5 | 5.5 | 0 | .0 | 7.5 |
| Aluminum | 0 | 0 | 0 | 0 | 3 |
| Vanadium | 0 | 0 | 0 | 0 | 3.2 |
| Silicon | 0.75 | 0.75 | 0.75 | 0.75 | 0.75 |
| Manganese | 0.75 | 0.75 | 0.75 | 0.75 | 0.75 |
| Carbon | 0.42 | 0 | 0 | 0 | 0 |
| Iron | 0 | 0 | 0 | 0 | 6.3 |
| Coefficient of Expansion | 14.09 | 14.37 | 14.7 | 14.5 | 13.8 |

In the above table, the alloy designated CC1 represents the basic chromium-cobalt alloy currently in use for removable partial dentures. Alloys numbered CC2, CC3 and CC4 show the effect of various changes in the formulation. For example, alloy CC2 shows that the removal of the carbon results in a still higher coefficient of expansion, though the material is softer and more easily workable. Both alloy CC1 and CC2 showed oxide discoloration. The alloy CC3 shows that the removal of molybdenum results in a still higher coefficient of expansion. A heavy cobalt oxide blue is also noted. In the case of alloy CC4, the elimination of the molybdenum and the reduction of the cobalt content resulted in formation of a purple oxide which is completely unacceptable. The coefficient of expansion remained high.

The composition in accordance with the invention, alloy CC5, in contrast, has a considerably lower coefficient of expansion. The overall composition had substantially little oxide formation and it was neither unacceptably hard nor embrittled. As a matter of fact, it is considerably softer, lower in fusion temperature, and consequently suffers less aftercasting shrinkage than those improved compositions containing tungsten, or with standard chromium-cobalt generally used for removable dentures.

The effect of the iron on the formulation is not totally clear. Its presence will be important to control hardness, fusion temperature, coefficient of expansion and chromium and cobalt oxidation by virtue of its effectively reducing the chromium and cobalt levels.

EXAMPLE 2

Using the alloy CC5 set forth in Example 1 above, a crown was formed and thereafter dental porcelain was adhered to it. The adhesion was performed at a temperature of 1800° F. After formation, the crown was inspected and it was noted that the adhesion between the alloy and the porcelain was acceptable. The crown fit well and no discoloration was noted. The finishing and polishing of the crown was comparable to that of conventional crowns not containing a combination of chromium and cobalt.

I claim:

1. A dental alloy consisting essentially of from 55 to 65% cobalt, 16 to 24% chromium, 6 to 8% molybdenum, and 2 to 4% each of aluminum and vanadium.
2. The dental alloy of claim 1, wherein the alloy also contains less than 1% each of silicon and manganese and less than 0.1% of carbon.
3. The dental alloy of claim 1, wherein the alloy also contains from 5 to 10% of iron.
4. A dental structure comprising the alloy of claims 1, 2 or 3 bonded to porcelain.

* * * * *